United States Patent [19]
Harper et al.

[11] Patent Number: 5,762,628
[45] Date of Patent: Jun. 9, 1998

[54] SAFETY SYRINGE WITH BREAKAWAY SEAL

[76] Inventors: Ronald G. Harper; Arlene P. Harper, both of 4860 Contento Cir., N. Las Vegas, Nev. 89031

[21] Appl. No.: 630,840

[22] Filed: Apr. 10, 1996

[51] Int. Cl.$^6$ .................................................. A61M 5/00
[52] U.S. Cl. .......................... 604/110; 604/195; 604/218; 604/240; 128/919
[58] Field of Search ............................. 604/110, 218, 604/195, 197, 198, 227, 228, 240, 241–243, 181, 187, 111, 220–222; 128/919

[56] References Cited

U.S. PATENT DOCUMENTS

| | | | |
|---|---|---|---|
| 4,906,231 | 3/1990 | Young | 604/228 |
| 4,976,693 | 12/1990 | Haast | 604/110 |
| 5,047,016 | 9/1991 | Dolgin et al. | 604/240 |
| 5,098,390 | 3/1992 | Wallingford | 604/195 |
| 5,205,827 | 4/1993 | Novacek et al. | 604/195 |
| 5,405,327 | 4/1995 | Chen | 604/110 |
| 5,415,646 | 5/1995 | Roth | 604/110 |
| 5,417,661 | 5/1995 | Stringer et al. | 604/110 |
| 5,458,576 | 10/1995 | Haber et al. | 604/195 |
| 5,496,278 | 3/1996 | Buff | 604/195 |

*Primary Examiner*—Michael Powell Buiz
*Assistant Examiner*—Ronald K. Stright, Jr.
*Attorney, Agent, or Firm*—Joseph N. Breaux

[57] ABSTRACT

A safety syringe including a hollow barrel member having a substantially cylindrical shaped plunger receiving cavity formed therethrough, the plunger receiving cavity terminating in a plunger receiving opening at a first end thereof and a cavity bottom member having a needle mounting portion at a second end thereof, the needle mounting portion being centrally oriented on the cavity bottom member and secured thereto by a breakaway plastic bridge seal, the needle mounting portion having a fluid port member having a cavity facing opening including at least one plunger engagement member extending from a defining sidewall thereof; and a plunger member having a plunger shaft a plunger bulb in connection with an end thereof that has a needle portion engagement member adapted to engage the plunger engagement member when the needle portion engagement member is inserted into the cavity facing opening. The resulting engagement between the needle portion engagement member and the plunger engagement member is of sufficient strength to allow a force generated by pulling on the plunger to cause the needle engagement portion to break free from the cavity bottom member by breaking the bond created by the breakaway bridge seal between the needle portion and the cavity bottom member.

6 Claims, 2 Drawing Sheets

SAFETY SYRINGE WITH BREAKAWAY SEAL

TECHNICAL FIELD

The present invention relates to disposable syringes for medical use and more particularly to a disposable syringe having a retractable hypodermic needle and safety cover.

BACKGROUND ART

With the spread of acquired immune deficiency syndrome (AIDS) it has become more important for health care workers to safely deal with patient blood and blood products. The danger of blood exposure is particularly apparent when injecting patients or taking blood samples with a hypodermic syringe. The primary danger is posed by the exposed hypodermic needle after the syringe has been used to administer medication. It would be desirable, therefore, to have a disposable syringe that included a mechanism for covering the hypodermic needle after the syringe has been used. It would be a further benefit if the needle covering mechanism could be actuated from behind the sharp needle point. It would be a further benefit if the needle could be withdrawn into the body of the syringe to prevent accidental punctures by the needle to janitorial personnel.

GENERAL SUMMARY DISCUSSION OF INVENTION

It is thus an object of the invention to provide a safety syringe that is disposable and that includes a mechanism for covering the hypodermic needle after the syringe has been used.

It is a further object of the invention to provide a safety syringe that includes a needle covering mechanism that is actuated from behind the sharp needle point.

It is a still further object of the invention to provide a safety syringe that includes a needle covering mechanism that withdraws the hypodermic needle into the body of the syringe.

It is a still further object of the invention to provide a safety syringe that accomplishes all or some of the above objects in combination.

Accordingly, a safety syringe is provided. The safety syringe comprises a hollow barrel member having a substantially cylindrical shaped plunger receiving cavity formed therethrough and defined by a cavity sidewall, the plunger receiving cavity terminating in a plunger receiving opening at a first end thereof and a cavity bottom member having a needle mounting portion at a second end thereof, the needle mounting portion being centrally oriented on the cavity bottom member and secured thereto by a breakaway bridge seal, the needle mounting portion having a fluid port member having a fluid passageway therethrough, the fluid passageway having a cavity facing opening and an exterior facing opening, and a needle engagement hub that protrudes from an exteriorly oriented surface of the needle mounting portion, the interiorly facing opening including at least one plunger engagement member extending from a defining sidewall thereof; and a plunger member having a plunger shaft having a thumb rest formed at one end thereof and a plunger bulb in connection with a second end thereof, the plunger bulb having bulb sidewalls adapted to sealing, slidingly engage the cavity sidewall of the plunger receiving cavity along the length thereof and a needle portion engagement member adapted to engage the plunger engagement member when the needle portion engagement member is inserted into the cavity facing opening, the engagement between the needle portion engagement member and the plunger engagement member being of sufficient strength to allow a force generated by pulling on the first plunger end to cause the needle mounting portion to break free from the cavity bottom member by breaking the bond created by the breakaway bridge seal between the needle mounting portion and the cavity bottom member.

BRIEF DESCRIPTION OF DRAWINGS

For a further understanding of the nature and objects of the present invention, reference should be had to the following detailed description, taken in conjunction with the accompanying drawings, in which like elements are given the same or analogous reference numbers and wherein.

EXEMPLARY MODE FOR CARRYING OUT THE INVENTION

Figure 1:
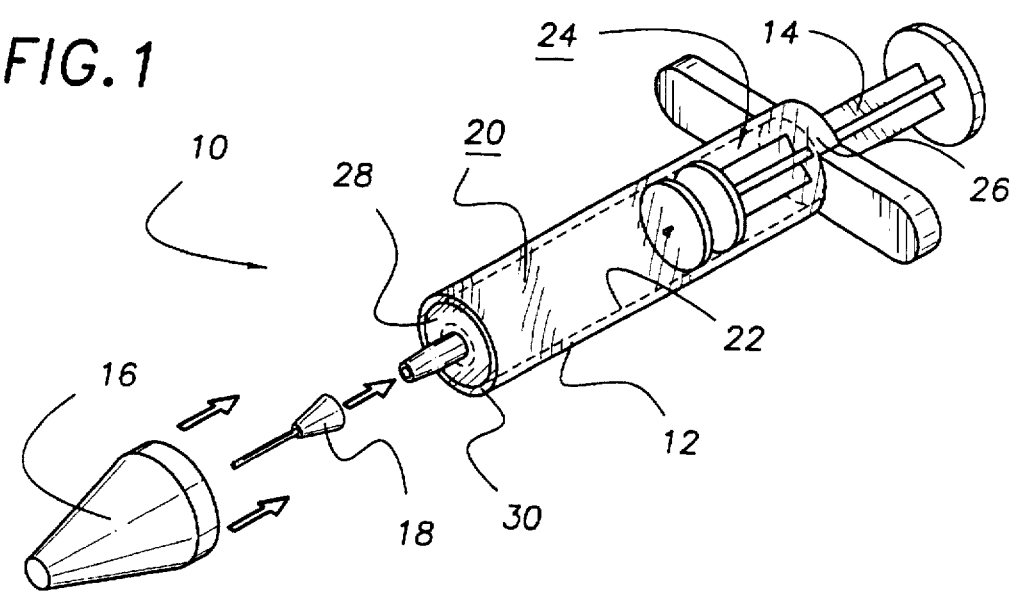
FIG. 1 is a perspective view of an exemplary embodiment of the safety syringe of the present invention with a representative hypodermic needle assembly and a disposal cover exploded away from the needle engagement hub located at the end of the syringe.
Figure 2:
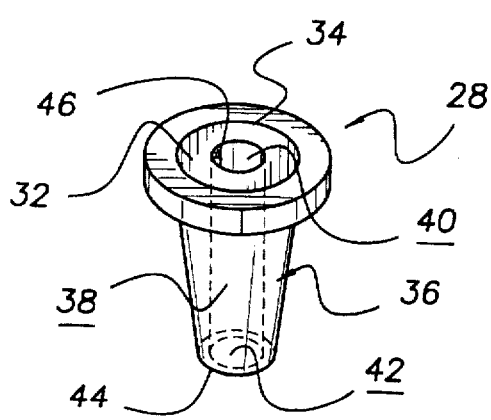
FIG. 2 is a detail perspective view of the cavity bottom member with the needle engagement portion sealed to the cavity bottom member with the breakaway plastic bride seal.

FIG. 1 shows an exemplary embodiment of the disposable safety syringe of the present invention generally designated by the numeral 10. Syringe 10 includes a hollow barrel member 12, a plunger member 14, and a safety cap 16. A conventional hypodermic needle assembly 18 is also included. Barrel member 12 is constructed from plastic and includes a cylindrical shaped plunger receiving cavity 20 that is defined by a cavity sidewall 22. Plunger receiving cavity 20 terminates in a plunger receiving opening 24 at a first end 26 thereof and a cavity bottom member 28 at a second end 30 thereof. With reference to FIG. 2, cavity bottom member 28 includes a needle mounting portion 32 centrally oriented thereon. Needle mounting portion 32 is secured to cavity bottom member by a breakaway plastic bridge seal 34.

Needle mounting portion 32 has a fluid port member 36 having a fluid passageway 38 formed therethrough. Fluid passageway 38 has a cavity facing opening 40 and an exterior facing opening 42. A needle engagement hub 44 is also provided for forming a sealing engagement hypodermic needle assembly 18. At least one rigid plunger engagement member 46 extends radially into cavity facing opening 40 of fluid passageway 38.

Figure 3:
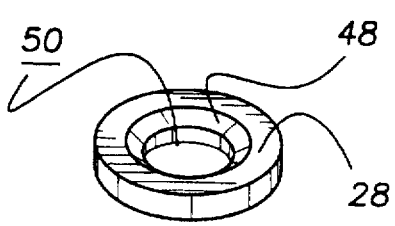
FIG. 3 is a detail perspective view of the cavity bottom portion with the needle engagement portion removed showing the beveled needle engagement portion holding lip.

FIG. 3 shows cavity bottom member 28 with needle engagement portion 32 removed to reveal a beveled needle engagement portion holding lip 48 defining a needle passageway 50 through cavity bottom member 28. Needle passageway 50 is sized sufficiently to allow the entire hypodermic needle assembly 18 to pass therethrough when needle engagement portion 32 is not in place.

Figure 4:
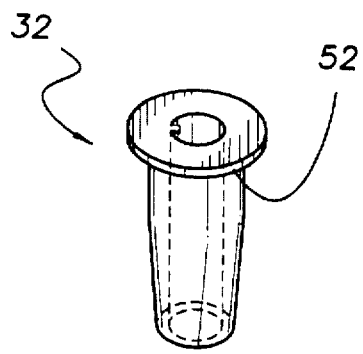
FIG. 4 is a detail perspective view of the needle engagement portion showing the beveled perimeter of the cavity bottom seat and the plunger engagement member extending outwardly from the defining sidewall of the cavity facing opening.

FIG. 4 shows needle engagement portion 32 in isolation. As shown needle engagement portion includes a beveled perimeter 52 adapted to seat within engagement portion holding lip 48. During assembly beveled perimeter 52 of engagement portion 32 is secured into connection with engagement portion holding lip 48 by a quantity of a plastic sealing adhesive. In this embodiment, the sealing adhesive forms breakaway bridge seal 34. However, it is contemplated by the inventors hereof that breakaway bridge seal 34 may be integrally formed between engagement portion 32 and cavity bottom member 28 during molding of barrel member 12.

Figure 5:
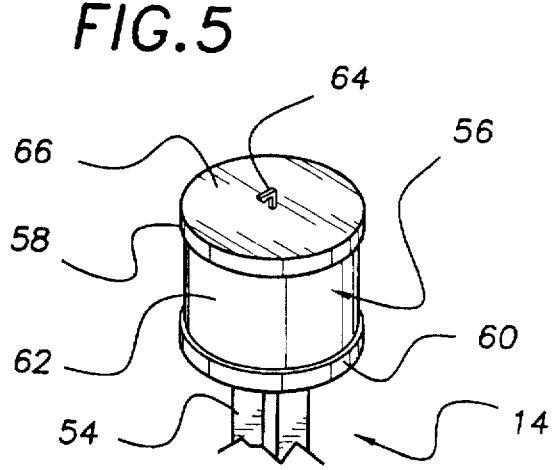
FIG. 5 is a detail perspective view of the plunger bulb member with the L-shaped needle portion engagement member extending from the piston head surface of the plunger bulb.

FIG. 5 is a detail perspective view of a second end section 54 of plunger member 14 with a plunger bulb 56 attached thereto. Plunger bulb 56 is constructed of resilient plastic and has a first and second cavity seal 58, 60 extending from a sidewall 62 thereof. First and second cavity seals 58, 60 sealing, slidingly engage cavity sidewall 22 of plunger receiving cavity 20 along the length thereof. A rigid, L-shaped needle portion engagement member 64 adapted to engage plunger engagement member 46 extends from a piston head surface 66 of plunger bulb 56. Needle portion engagement member 64 is positioned on piston head surface 66 in a manner such that needle portion engagement member is positioned within cavity facing opening 40 when piston head surface 66 is in contact with cavity bottom member 28.

Figure 6:
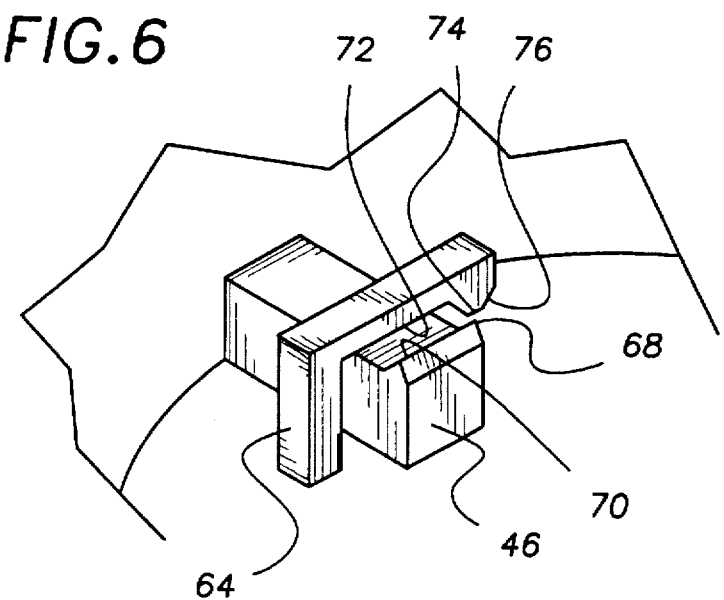
FIG. 6 is a detail perspective view showing the L-shaped needle portion engagement member extending from the piston head surface of the plunger bulb in engagement with plunger engagement member extending outwardly from the defining sidewall of the cavity facing opening.

FIG. 6 is a detail perspective view of L-shaped needle portion engagement member 64 in engagement with plunger engagement member 46. Plunger engagement member 46 includes a first securing lip 68 at a distal end of a substantially planar contact surface 70. Needle portion engagement member 64 has a substantially planar contact surface 72 terminating at a distal end thereof with a second securing lip 74 extending away therefrom. A beveled leading edge 76 is provided at the far end of second securing lip 74 to assist engagement between needle portion engagement member 64 and plunger engagement member 46 by forcing second securing lip 74 around contact surface 70 during engagement of needle portion engagement member 64 and plunger engagement member 46.

Figure 7:
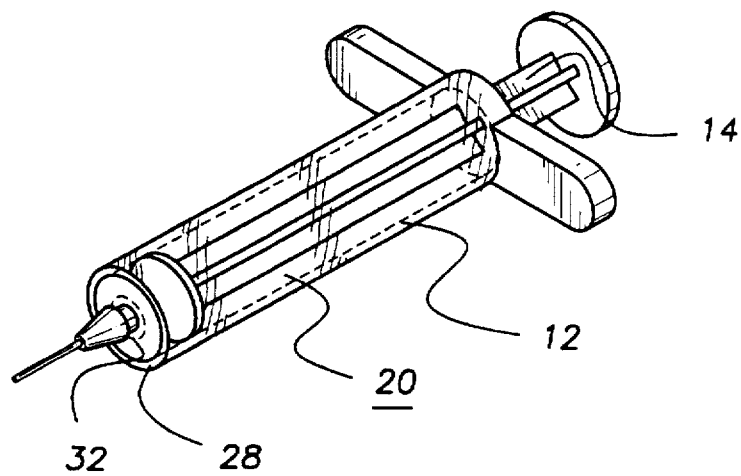
FIG. 7 is a perspective view of the safety syringe of FIG. 1 with the representative hypodermic needle assembly secured to the needle engagement hub with the plunger member fully inserted into the plunger receiving cavity.

With reference to FIG. 7, engagement between needle portion engagement member 64 and plunger engagement member 46 is accomplished by pushing plunger member 14 into plunger receiving cavity 20 until piston head surface 66 (FIG. 5) contacts cavity bottom member 28 and needle portion engagement member 64 is positioned within cavity facing opening 40 (FIG. 6). Plunger member 14 is then rotated counter clockwise with respect to barrel member 12 until beveled leading edge 76 contacts plunger engagement member 46 forcing second securing lip 74 around contact surface 70. Once securing lip 74 is positioned past contact surface 70 of plunger engagement member 46, plunger 14 is locked to needle engagement portion 32. Continuing to rotate plunger member 14 in the counterclockwise direction breaks breakaway bridge seal 34 disengaging needle mounting portion 32 from cavity bottom member 28.

Figure 8:
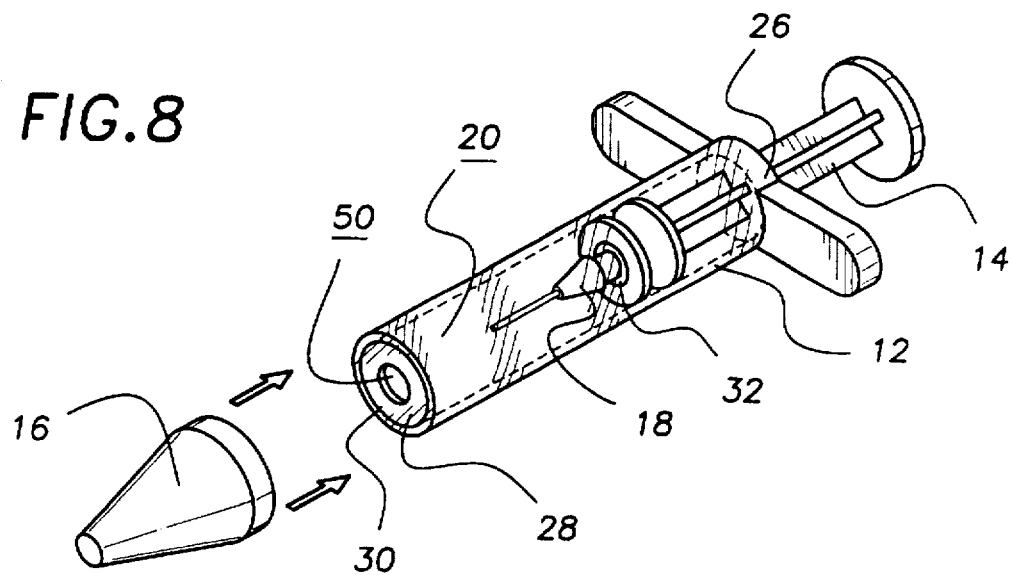
FIG. 8 is a perspective view of the safety syringe of FIG. 1 with the needle engagement portion affixed to the plunger bulb and the needle engagement portion broken free from the cavity bottom member.

With reference to FIG. 8, once needle mounting portion 32 is disengaged from cavity bottom member 28, plunger member 14 is withdrawn toward first end 26 of barrel member 12. As plunger member 14 travels toward first end 26 needle assembly 18 is pulled through needle passageway 50 of cavity bottom member 28 and into plunger receiving cavity 20 shielding the user from further possible contact with needle assembly 18. For additional protection, after needle assembly 18 is positioned entirely within plunger receiving cavity 20, safety cap 16 is placed over second end 30 of barrel member 12.

It can be seen from the preceding description that a safety syringe has been provided that is disposable; and that includes a mechanism for covering the hypodermic needle after the syringe has been used, that is actuated from behind the sharp needle point, and that withdraws the hypodermic needle into the body of the syringe.

It is noted that the embodiment of the safety syringe described herein in detail for exemplary purposes is of course subject to many different variations in structure, design, application and methodology. Because many varying and different embodiments may be made within the scope of the inventive concept(s) herein taught, and because many modifications may be made in the embodiment herein detailed in accordance with the descriptive requirements of the law, it is to be understood that the details herein are to be interpreted as illustrative and not in a limiting sense.

What is claimed is:

1. A safety syringe comprising:

a hollow barrel member having a substantially cylindrical shaped plunger receiving cavity formed therethrough and defined by a cavity sidewall, said plunger receiving cavity terminating in a plunger receiving opening at a first end thereof and a cavity bottom member having a needle mounting portion at a second end thereof, said needle mounting portion being centrally oriented on said cavity bottom member and secured thereto by a breakaway plastic bridge seal, said needle mounting portion having a fluid port member having a fluid passageway therethrough, said fluid passageway having a cavity facing opening and an exterior facing opening, and a needle engagement hub that protrudes from an exteriorly oriented surface of said needle mounting portion, said interiorly facing opening including at least one plunger engagement member extending from a defining sidewall thereof; and a plunger member having a plunger shaft having a thumb rest formed at one end thereof and a plunger bulb in connection with a second end thereof, said plunger bulb having bulb sidewalls adapted to sealing, slidingly engage said cavity sidewall of said plunger receiving cavity along said length thereof and a needle portion engagement member adapted to engage said at least one plunger engagement member when said needle portion engagement member is inserted into said cavity facing opening, said engagement between said needle portion engagement member and said at least one plunger engagement member being of sufficient strength to allow a force generated by pulling on said first plunger end to cause said needle engagement portion to break free from said cavity bottom member by breaking said bond created by said breakaway bridge seal between said needle mounting portion and said cavity bottom member.

2. The safety syringe of claim 1, wherein:

said cavity bottom member includes a beveled needle engagement portion holding lip defining a needle passageway therethrough, said needle mounting portion includes a beveled perimeter adapted to seat within said engagement portion holding lip; and said breakaway plastic bridge seal is located between said cavity bottom member beveled needle engagement portion holding lip and said needle mounting portion beveled perimeter.

3. The safety syringe of claim 2, wherein:

said breakaway bridge seal is formed from an adhesive positioned between said beveled needle engagement portion holding lip and said beveled perimeter of said needle engagement portion.

4. The safety syringe of claim 3 wherein:

said needle portion engagement member is substantially L-shaped and has a substantially planar contact surface terminating at a distal end thereof with a securing lip that extends away therefrom, and a beveled leading edge is provided adjacent said securing lip.

5. The safety syringe of claim 2 wherein:

said needle portion engagement member is substantially L-shaped and has a substantially planar contact surface terminating at a distal end thereof with a securing lip that extends away therefrom, and a beveled leading edge is provided adjacent said securing lip.

6. The safety syringe of claim 1 wherein:

said needle portion engagement member is substantially L-shaped and has a substantially planar contact surface terminating at a distal end thereof with a securing lip that extends away therefrom, and a beveled leading edge is provided adjacent said securing lip.

* * * * *